(12) United States Patent
Yi

(10) Patent No.: US 11,701,675 B2
(45) Date of Patent: Jul. 18, 2023

(54) DISPENSING DEVICE

(71) Applicant: IZER29, LLC, Compton, CA (US)

(72) Inventor: Jason Yi, Los Angeles, CA (US)

(73) Assignee: IZER29, LLC, Compton, CA (US)

( * ) Notice: Subject to any disclaimer, the term of this patent is extended or adjusted under 35 U.S.C. 154(b) by 0 days.

(21) Appl. No.: 17/521,741

(22) Filed: Nov. 8, 2021

(65) Prior Publication Data

US 2022/0143637 A1    May 12, 2022

Related U.S. Application Data

(60) Provisional application No. 63/110,583, filed on Nov. 6, 2020.

(51) Int. Cl.
| | | |
|---|---|---|
| *B05B 11/00* | (2023.01) | |
| *A61L 2/26* | (2006.01) | |
| *A61L 2/00* | (2006.01) | |
| *B05B 11/10* | (2023.01) | |

(52) U.S. Cl.
CPC ........ *B05B 11/0054* (2013.01); *A61L 2/0088* (2013.01); *A61L 2/26* (2013.01); *B05B 11/1001* (2023.01); *A61L 2202/15* (2013.01)

(58) Field of Classification Search
CPC ............. B05B 11/0054; B05B 11/3001; B05B 11/0038; B05B 11/3052; A61L 2/0088; A61L 2/26; A61L 2202/15; A61L 2/18; A47K 5/12; A47K 5/1205
See application file for complete search history.

(56) References Cited

U.S. PATENT DOCUMENTS

| | | | | |
|---|---|---|---|---|
| 6,983,864 | B1 * | 1/2006 | Cagle | ................. B05B 11/0005 222/321.9 |
| 7,134,577 | B1 * | 11/2006 | Verma | ................. B05B 11/0038 222/105 |

FOREIGN PATENT DOCUMENTS

JP            H970371 A    *    3/1997    ......... B05B 11/3001

* cited by examiner

*Primary Examiner* — Donnell A Long
(74) *Attorney, Agent, or Firm* — Avyno Law P.C.

(57) ABSTRACT

The invention relates to a dispensing device comprising a dispensing case that may house a dispensing cartridge, where the dispensing cartridge holds a liquid to be dispensed. The dispensing device further comprising a top cap, an actuator, a main body and a bottom cap, where the main body is positioned between the top cap and the bottom cap. The dispensing device further comprising top and bottom magnets that magnetically repel one another. Upon pressing of the actuator, material from the dispensing cartridge is dispensed and upon releasing of the actuator, the magnetic repellency of the top and bottom magnets moves the actuator back to its original position.

19 Claims, 10 Drawing Sheets

DISPENSING DEVICE

FIELD OF THE INVENTION

This invention relates to a dispensing device and a method for dispensing a variety of different types of dispensing materials.

BACKGROUND OF THE INVENTION

The medical community has determined that the spread of germs and viruses are a main cause of many illnesses. Therefore, in an attempt to curtail the spread of these illness-causing germs, the use of hand sanitizers (particularly easy to carry hand sanitizers) has become much more commonplace today.

However, traditional carry-on hand sanitizers are bulky, messy, clog and malfunction quite quickly and often. Therefore, a need exists for a minimally-sized dispensing device and/or case that is not only antimicrobial, ergonomic and stylish but can also be easily slipped into a shirt pocket, or present a slim profile in a pants pocket or purse and that will be highly durable.

Additionally, many traditional dispensing devices utilize spring mechanisms for pumping and dispensing liquids, creams or gels contained therein. Such spring mechanisms can be hard to pump, wear quickly over time and malfunction often. Particularly, the spray nozzles of many atomizers or spraying cartridges become clogged and eventually stop working or do not provide a fine mist. Therefore, a need also exists for a dispensing device that can accommodate a recyclable and easily replaceable dispensing cartridge (e.g., spray cartridge) that aids in providing an effortless, smooth pump action for dispensing a liquid without the use of any springs or other easily malfunctioning mechanisms that can wear with time.

SUMMARY OF THE INVENTION

The present application relates to a dispensing device and a method for dispensing a variety of different types of dispensing materials.

In one example, the dispensing device may comprise of a dispensing case that houses a dispensing cartridge. The dispensing case may have a top end and bottom end. A dispensing case actuator may be located at the top end and a top magnet may be operatively attached to the dispensing case actuator. A bottom magnet may attach to the dispensing case and may be aligned with the top magnet. The top and bottom magnets may magnetically repel one another. The dispensing cartridge may comprise of a dispensing cartridge actuator operatively connected to a pump mechanism for dispensing liquid held within the dispensing cartridge. The actuation of the dispensing case actuator from a first position to a second position may actuate the dispensing cartridge actuator from a first position to a second position to dispense the liquid in the dispensing cartridge.

An example of a dispensing case is also provided. The dispensing case may comprise of a main body having a top end and bottom end and an actuator. A top magnet may operatively attach to the actuator and a bottom magnet may attach to the main body. The top magnet may be aligned with and magnetically repel the bottom magnet.

A method for dispensing a material is also provided. The method may comprise of providing a dispensing case having a top end and bottom end and a dispensing case actuator that moves between a first position and second position. The dispensing case may house a dispensing cartridge holding a dispensing material. The dispensing cartridge may comprise of a dispensing cartridge actuator. The dispensing case actuator may operate with the dispensing cartridge actuator. A top magnet may be connected to the dispensing case actuator and a bottom magnet may be attached to the dispensing case and may be aligned with and magnetically repel the top magnet. The next step of the method may comprise of moving the dispensing case actuator from the first position to the second position. Moving the dispensing case actuator from the first position to the second position would also move the dispensing cartridge actuator from a first position to a second position for dispensing the dispensing material. Additionally, when releasing the dispensing case actuator, the magnetic repellency between the top magnet and bottom magnet causes the dispensing case actuator to move from the second position back to the first position.

Other devices, apparatus, systems, methods, features and advantages of the invention will be or will become apparent to one with skill in the art upon examination of the following figures and detailed description. It is intended that all such additional systems, methods, features and advantages be included within this description, be within the scope of the invention, and be protected by the accompanying claims.

BRIEF DESCRIPTION OF THE FIGURES

The invention may be better understood by referring to the following figures. The components in the figures are not necessarily to scale, emphasis instead being placed upon illustrating the principles of the invention. In the figures, like reference numerals designate corresponding parts throughout the different views.

DETAILED DESCRIPTION

Figure 1:
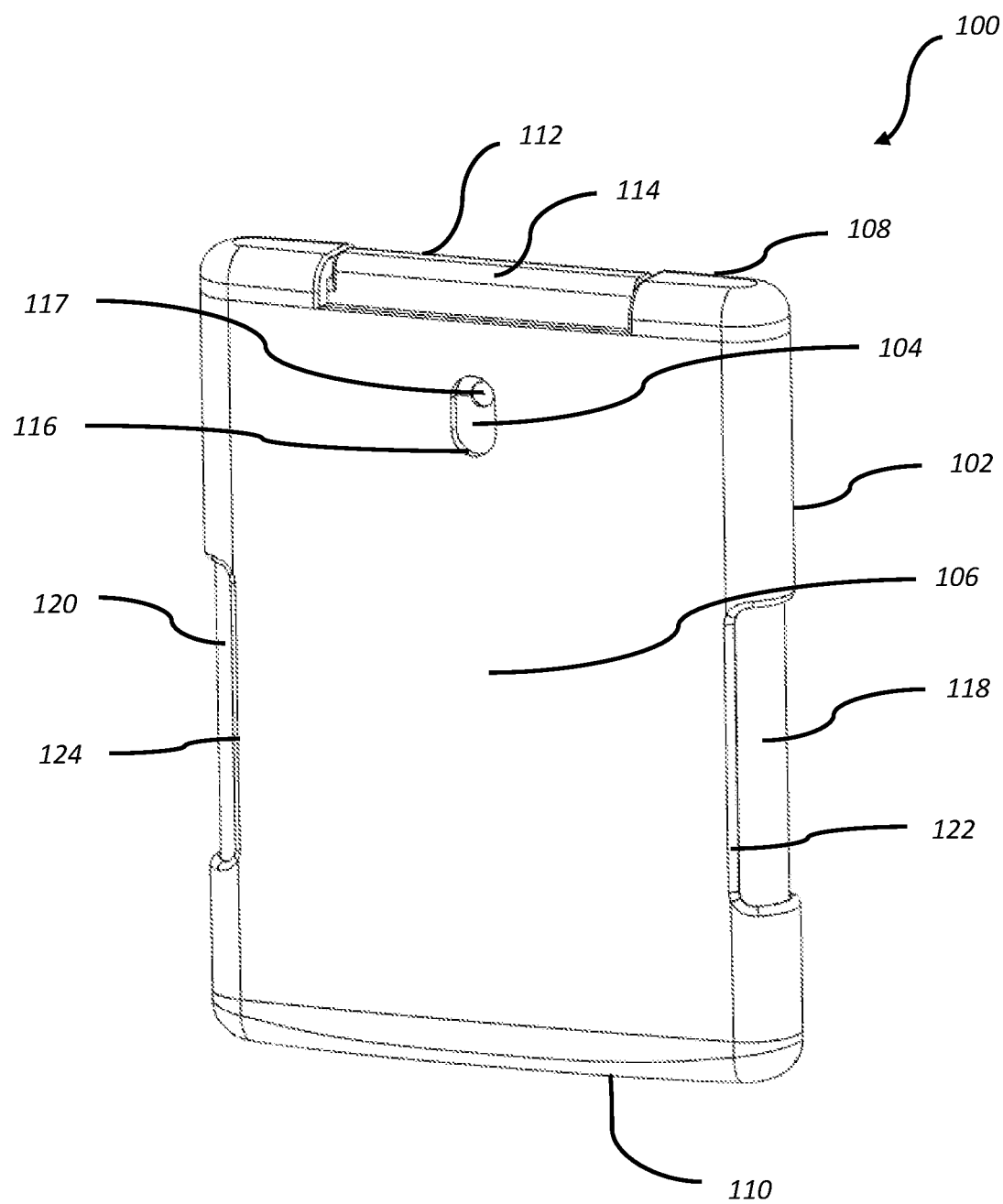
FIG. 1 is a front perspective view of one example of the dispensing device of the present invention.

Referring now to the drawings, examples of the dispensing device of the present invention are illustrated in FIGS.

1-12. As referred to herein, the term "dispensing" as used throughout herein shall be accorded the broadest reasonable interpretation. The types of dispensing as disclosed herein shall include, but is not limited to, spraying or misting. Therefore, the term "spraying" may be used interchangeably with the term "dispensing." It should also be understood that the all of various parts or components discussed herein may be integrated with one another in any combination or may be separate parts attached to one another. It will be further understood that various aspects or details of the invention may be changed without departing from the scope of the invention. Furthermore, the foregoing description is for the purpose of illustration only, and not for the purpose of limitation—the invention being defined by the claims.

FIG. 1 is a front perspective view of one example of the dispensing device 100 of the present invention. As illustrated in FIG. 1, the dispensing device 100 comprises of a dispensing case 102 and a dispensing cartridge 104, where the dispensing case 102 houses the dispensing cartridge 104.

As shown in FIGS. 1-12, one example of the shape and size of the dispensing device 100 is that it may be similar to a rectangle or square and may lay generally flat, similar to a credit card or mobile electronic device such as a smart phone (e.g., iPhone). One of the purposes of having dispensing device 100 be of a generally flat and compact shape and size is to make it easier for a user to carry dispensing device 100, whether in pockets, purses or carrying bags. In one example, dispensing device 100 may be approximately 3-7 inches in length, 2-5 inches in width, and 0.3-1 inch in thickness (or most preferably approximately 3.5-4.5 inches in length, 2.75-3.75 inches in width, and 0.4-0.8 inches in thickness). It should further be understood that the dispensing device 100 may be of any size or shape without departing from the scope of the invention.

As shown in FIGS. 1-12, the dispensing device 100 comprises of a dispensing case having a top end having a top cap 112, a bottom end having a bottom cap 110, an actuator 112 and at least one top magnet 318, 320 and at least one bottom magnet 322, 324 positioned on the left and right sides of the device 100. Actuator 112 may be referred to herein as dispensing case actuator.

In its simplest form, the body of the dispensing case 102 comprises of a main body 106 having a top end and bottom end, where a top cap 108 is located on the top end and a bottom cap 110 is located on the bottom end. The main body 102 is positioned between the top cap 108 and bottom cap 110 and includes a dispense slot or opening 116 on its front surface that is aligned with the dispense hole 117 of dispensing cartridge 104. While the main body 106, top cap 108 and bottom cap 110 are shown as separate parts, it should be understood that such parts may be integrated with one another in any combination.

With respect to the material of the dispensing case 102, namely the main body 106, top cap 108 and a bottom cap 110, while any material known in the art may be utilized (including but not limited to plastic, carbon fiber, gun metal, aluminum, gold, silver, copper etc.), the dispensing case 102 shown and described herein utilizes copper and/or its alloys (including but not limited to brasses, bronzes, cupronickel, copper-nickel-zinc etc.). The reason why copper and/or its alloys are utilized is because such metals are naturally anti-microbial. In fact, it is well known in the art that bacteria, yeasts, and viruses may be rapidly killed on metallic copper surfaces and studies show that copper is found to inactivate antimicrobial resistant bugs, even copper-resistant microbes. Therefore, in one example, the dispensing case 102 of the present invention may comprise of 99.9% pure copper. Incorporating such copper material allows the dispensing case 102 to not only be made of a naturally sanitizing material but will also allow the dispensing case 102 to last for an extended period of time given that copper does not rust. Furthermore, because the dispensing device 100 may be utilized as a hand sanitizer, utilizing copper as the material for the dispensing case 102 enhances the overall sanitization or decontamination properties of dispensing device 100.

As shown in FIG. 1 the dispensing case 102 also includes an actuator 112, where the actuator 112 includes a pushbutton 114 exposed by an opening in the top cap 108. The actuator may also be integrated with the main body 106 of the dispensing case 102.

The dispensing case 102 also comprises of tubes 118, 120 that extend between the top cap 108 and bottom cap 110 and are positioned on the left and right sides of the dispensing case 102. Such tubes 118, 120 may be housed within channels on the left and right sides of the dispensing case 102 and may also be integrated with the main body 106. Furthermore, while two tubes are shown, it should be understood that any number of tubes may be utilized in connection with the present invention. For example, the dispensing case 102 may comprise of only one tube.

Tubes 118, 120 run parallel to one another and may be made of any transparent or semi-transparent material known in the art, including but not limited to acrylic or glass. In other examples, the tubes 118, 120 may be made of any opaque material known in the art. One end of the tubes 118, 120 may attach to actuator 112 while the opposing end of tubes 118, 120 may attach to bottom cap 110. Such attachment can be made via any mechanical means known in the art, including but not limited to, friction fit, press fit, screws, clips, or magnets. Alternatively, tubes 118, 120 may attach to actuator 112 and bottom cap 110 via any mechanical means known in the art via any adhesive means known in the art, including but not limited to glue, sonic welding, or insert molding.

The left and right sides of the main body 102 may include openings 122, 124, to allow visibility of the tubes 118, 120 from the exterior of dispensing case 102.

Figure 2:
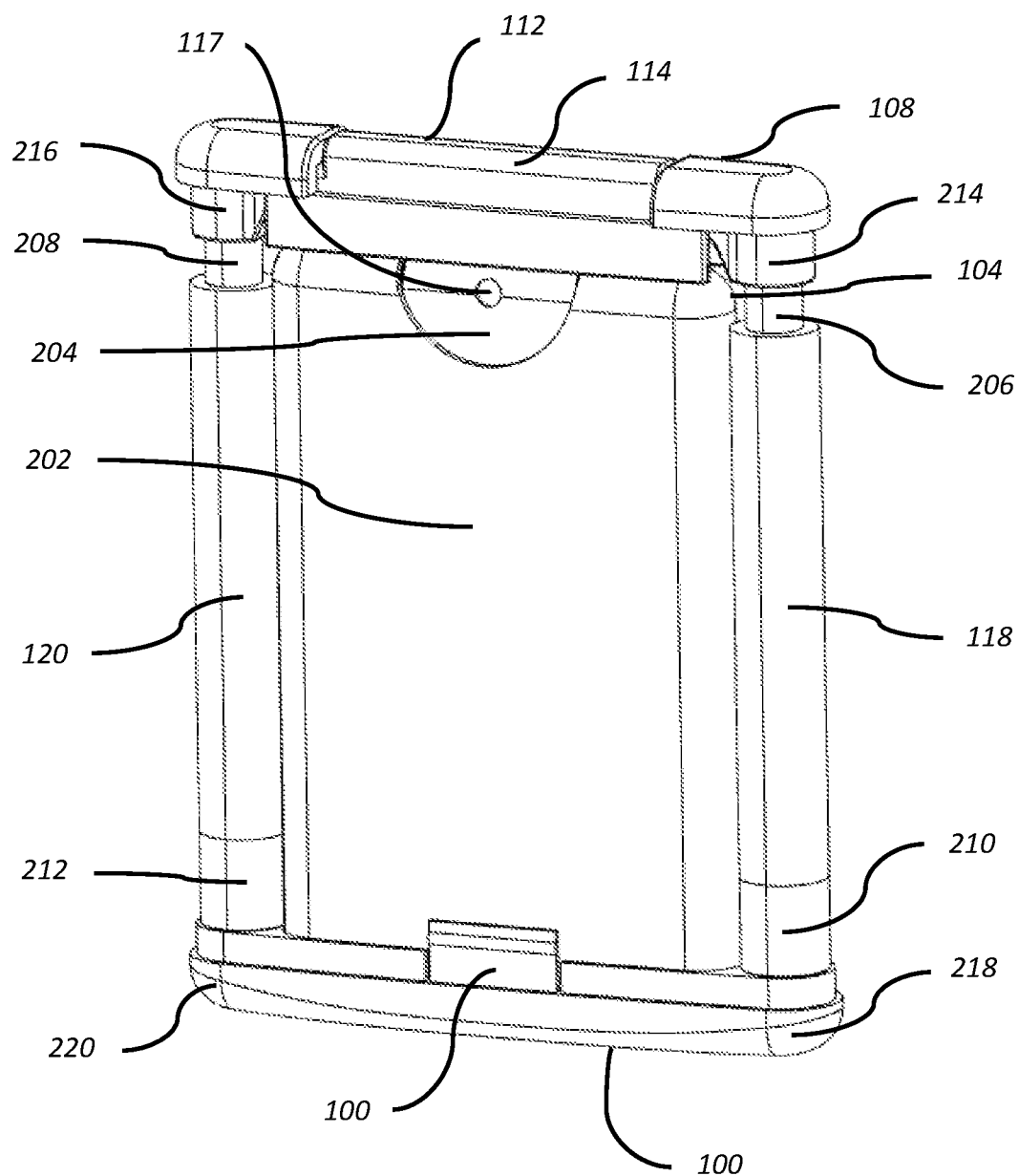
FIG. 2 is a front perspective view of the dispensing device of FIG. 1 where the main body of the dispensing case is removed.

FIG. 2 is a front perspective view of the dispensing device 100 of FIG. 1 where the main body 106 of the dispensing case 102 is removed. As shown, dispensing cartridge 104 is positioned within dispensing case 102. Dispensing cartridge 104 comprises of a main body 202 and an actuator 204. In one example, the main body 202 may hold a reservoir of liquid to be sprayed upon actuation (e.g., pressing down) of actuator 204. Such actuation is illustrated by arrow A in FIG. 10B.

Also shown in FIG. 2, are top posts 206, 208, bottom posts 210, 212, actuator 112 having a first end 214 and opposing second end 216 and the bottom cap 110 having a first end 218 and opposing second end 220. Top posts 206, 208 and bottom posts 210, 212 may be integrated with main body 106 of dispensing case 102. Each top and bottom post includes a first end and an opposing second end. The first end 302 of top post 206 attaches to the first end 214 of actuator 112 while first end 304 of top post 208 may attach to the opposing second end 216 of actuator 112. The first end 314 of bottom post 210 may attach to the first end 218 of the bottom cap 110 while first end 316 of bottom post 212 may attach to the opposing second end 220 of bottom cap 110. Top posts 206, 208 may attach to the ends 214, 216 of actuator 112 via any mechanical means known in the art, including but not limited to, friction fit, press fit, screws, clips, or magnets. Alternatively, top posts 206, 208 may attach to the ends 214, 216 of actuator 112 via any adhesive means known in the art, including but not limited to glue, sonic welding, or insert molding.

Similarly, bottom posts 210, 212 may attach to the ends 218, 220 of bottom cap 110 via any mechanical means known in the art, including but not limited to, friction fit, press fit, screws, clips, or magnets. Alternatively, first ends of bottom posts 210, 212 may attach to the ends 218, 220 of bottom cap 110 via any adhesive means known in the art, including but not limited to glue, sonic welding, or insert molding. FIG. 2 also shows bottom cap 110 optionally having a clip 222 for securing bottom cap 110 to main body 106.

Figure 3:
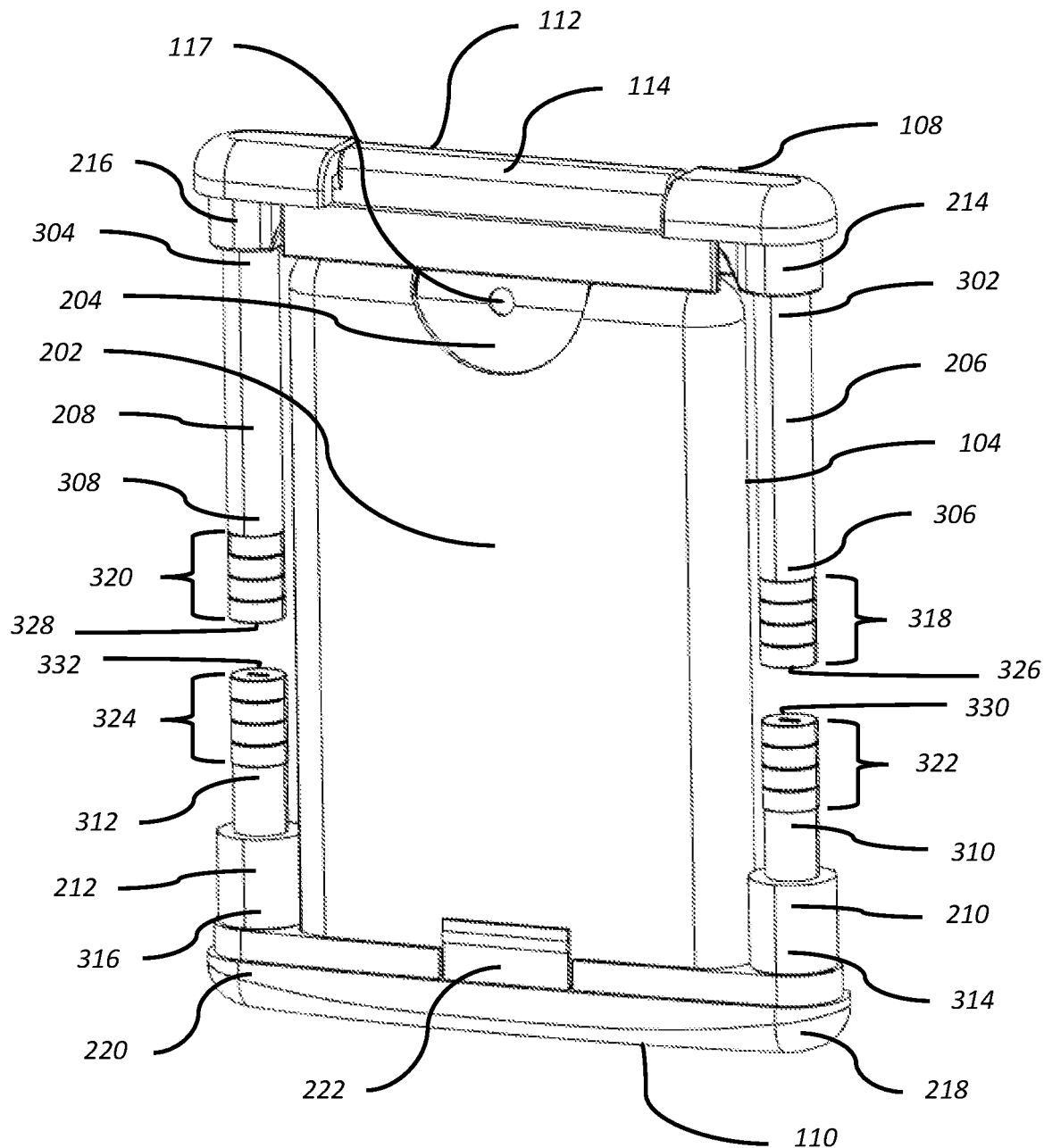
FIG. 3 is a front perspective view of the dispensing device of FIG. 2 where the tubes of the dispensing case are removed.

FIG. 3 is a front perspective view of the dispensing device of FIG. 1 where the main body 106 and tubes 118, 120 of the dispensing case 102 are removed. FIG. 3 illustrates the first ends 302, 304 of top posts 206, 208 attached to the first and second ends 214, 216 of actuator 112 and the first ends 314, 316 of bottom posts 210, 212, attached to the first and second ends 218, 220 of bottom cap 110. FIG. 3 also illustrates the second ends 306, 308 of top posts 206, 208 attached to top magnets 318, 320 and the second ends 310, 312 of bottom posts 210, 212 attached to bottom magnets 322, 324. Top and bottom magnets 318, 320, 322, 324 may attach, respectively, to top and bottom posts 206, 208, 210, 212 via any mechanical means known in the art, including but not limited to, friction fit, press fit, screws, clips, or magnets or via any adhesive means known in the art, including but not limited to glue, sonic welding, or insert molding. While FIG. 3 shows top magnets 318, 320 attach to actuator 112 via top posts 206, 208, it should be understood that in other examples, top magnets 318, 320 may operatively attach directly or indirectly to actuator 112 via any mechanical or adhesive means discussed herein.

Similarly, while FIG. 3 shows bottom magnets 322, 324 attach to bottom cap 110 via bottom posts 210, 212, it should be understood that in other examples, bottom magnets 322, 324 may attach directly or indirectly to bottom cap 110 via any mechanical or adhesive means discussed herein. Additionally, it should be understood that top magnets 318, 320 may operatively attach directly or indirectly to any area on actuator 112 and bottom magnets 322, 324 may attach directly or indirectly to any area on dispensing case 102, including but not limited to main body 106. In other words, bottom magnets 322, 324 are not limited to only attaching to the bottom end of main body 106 or the bottom cap 110. In other examples, bottom magnets 322, 324 may be integrated with main body 106.

As is well known in the art, all magnets have north and south poles. Opposite poles are attracted to each other, while the same poles repel each other. In the present case, the ends 326, 328 of top magnets 318, 320 that face the ends 330, 332 of bottom magnets 322, 324 are of the same poles. In other words, top magnet 318 aligns with and magnetically repels bottom magnet 322 while top magnet 320 aligns with and magnetically repels bottom magnet 324. It should be further understood that while the dispensing device 100 shows two pairs of top magnets and bottom magnets, any number of pairs of top magnets and bottom magnets may be utilized in connection with the present invention. For example, the present invention may utilize only one top magnet that is aligned with and magnetically repels only one bottom magnet.

In operation, upon a user pressing down on push-button 114 of actuator 112, top magnets 318, 320 will be pushed towards magnetically opposing bottom magnets 322, 324 and when push-button 114 of actuator 112 is released, the actuator 114 will spring back up due to the magnetic repellency between top magnets 318, 320 and bottom magnets 322, 324. Upon pressing or pushing down on actuator 112, actuator 204 of the dispensing cartridge 104 will also be pressed or pushed down, thereby allowing the material in the dispensing cartridge 104 to be dispensed out through dispense hole 117 and dispense slot 116. The benefits of incorporating the magnetic mechanism described herein is to provide greater durability to dispensing device 100 and to allow a much smoother actuation movement of actuator 112 due to the frictionless magnetic field created between top and bottom magnets 318, 320, 322, 324. Actuator 204 may be referred to herein as dispensing cartridge actuator.

Figure 4:
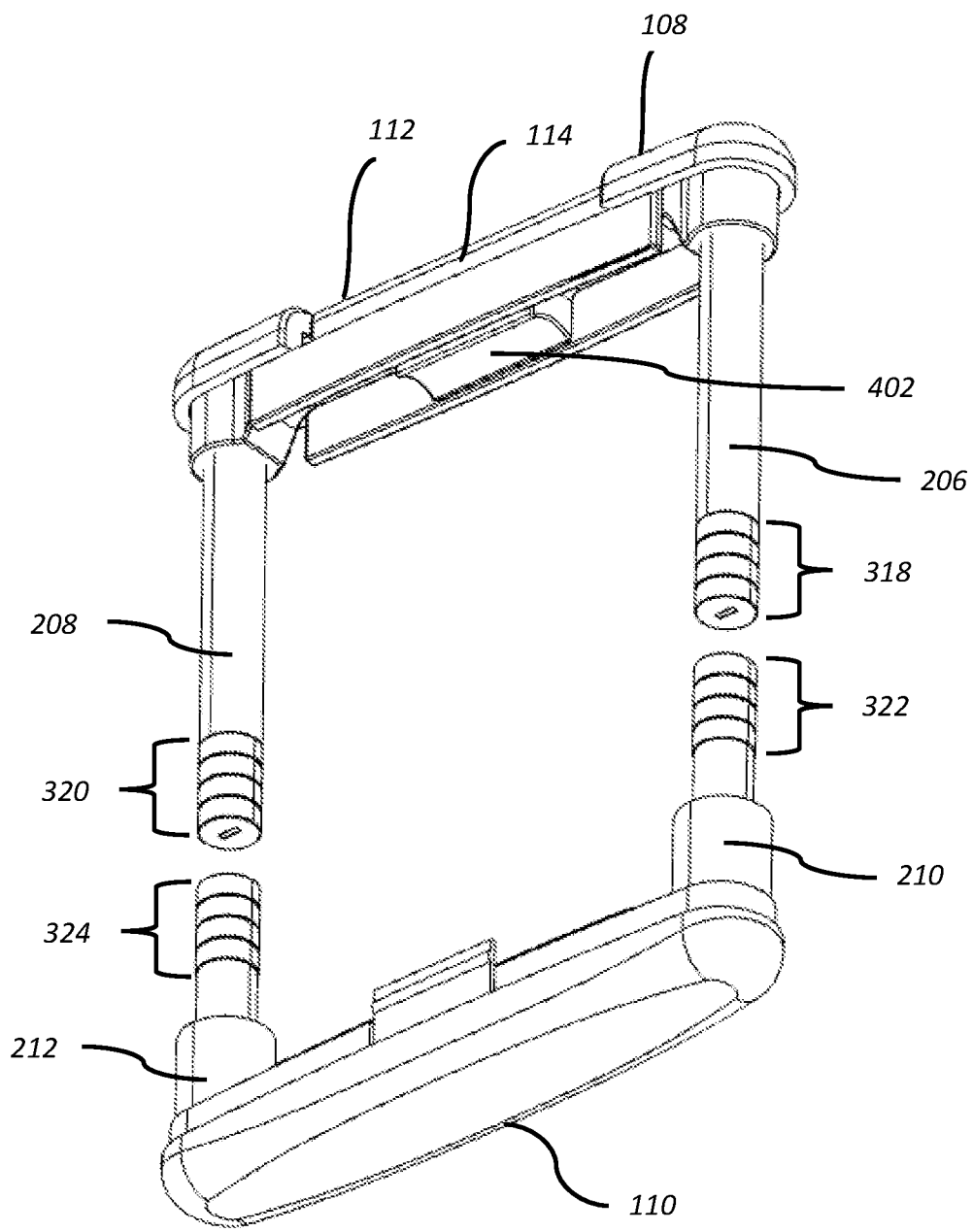
FIG. 4 is a bottom perspective view of the dispensing device of FIG. 3 where the dispensing cartridge is removed.

FIG. 4 is a bottom perspective view of the dispensing device 100 of FIG. 1 where the main body 106 and tubes 118, 120 of the dispensing case 102 and the dispensing cartridge 104 are removed. FIG. 4 shows the bottom of actuator 112 comprising an engagement tab 402 that engages with the actuator 204 of dispensing cartridge 104. As stated above, upon pressing or pushing down on actuator 112, engagement tab 402 will press down on actuator 204 of the dispensing cartridge 104, thereby dispensing the material in the dispensing cartridge 104 to be dispensed out through dispense hole 117 and dispense slot 116.

Figure 5:
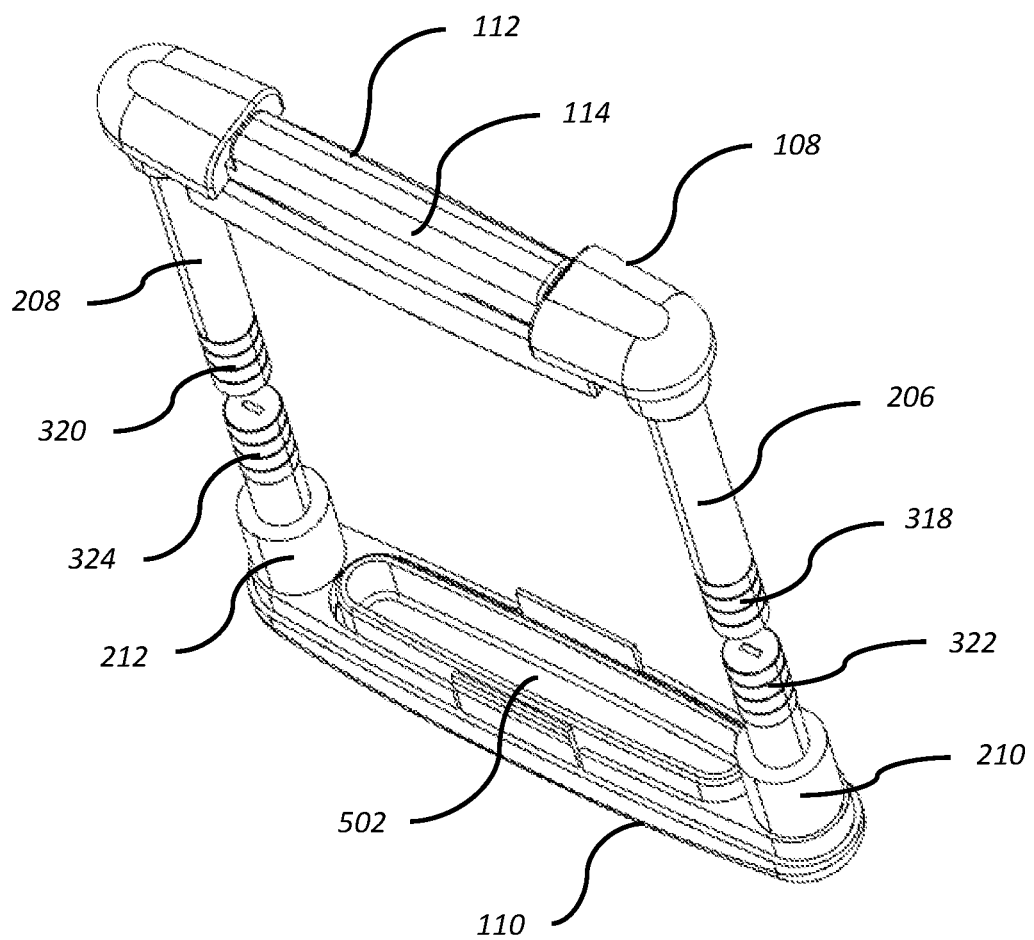
FIG. 5 is a top perspective view of the dispensing device of FIG. 4.

FIG. 5 is a top perspective view of the dispensing device 100 of FIG. 1 where the main body 106 and tubes 118, 120 of the dispensing case 102 and the dispensing cartridge 104 are removed. FIG. 5 shows the top of bottom cap 110 comprising a groove 502 that may receive the bottom of dispensing cartridge 104 to better secure dispensing cartridge 104 within dispensing case 102.

Figure 6:
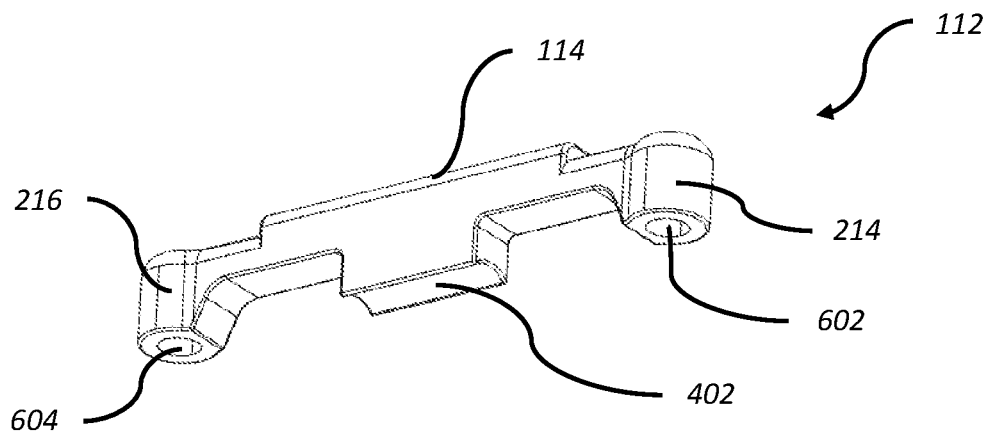
FIG. 6 is a bottom perspective view of the actuator of the dispensing case of FIG. 1.

FIG. 6 is a bottom perspective view of the actuator 112 of the dispensing case 102 of FIG. 1. In particular, FIG. 6 shows holes 602, 604 that may be incorporated on the bottom of the first and second ends 214, 216 of actuator 112. Such holes 602, 604 may receive posts 206, 208 to better secure posts 206, 208 to actuator 112.

Figure 7:
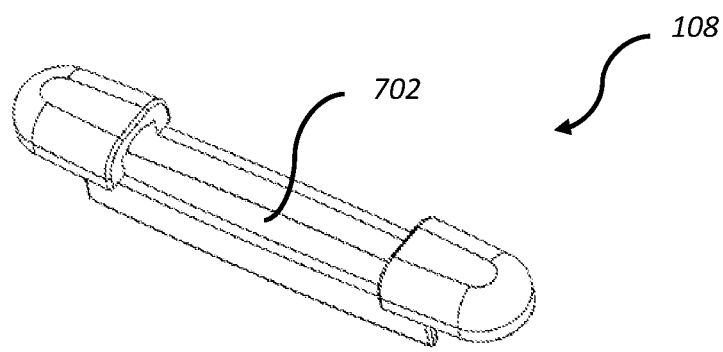
FIG. 7 is a top perspective view of the top cap of the dispensing case of FIG. 1.

FIG. 7 is a top perspective view of the top cap 108 of the dispensing case 102 of FIG. 1. In particular, FIG. 7 shows top cap 108 comprising an opening 702 for exposing the push-button 114 of actuator 112, thereby allowing a user access to actuate push-button 114.

Figure 8:
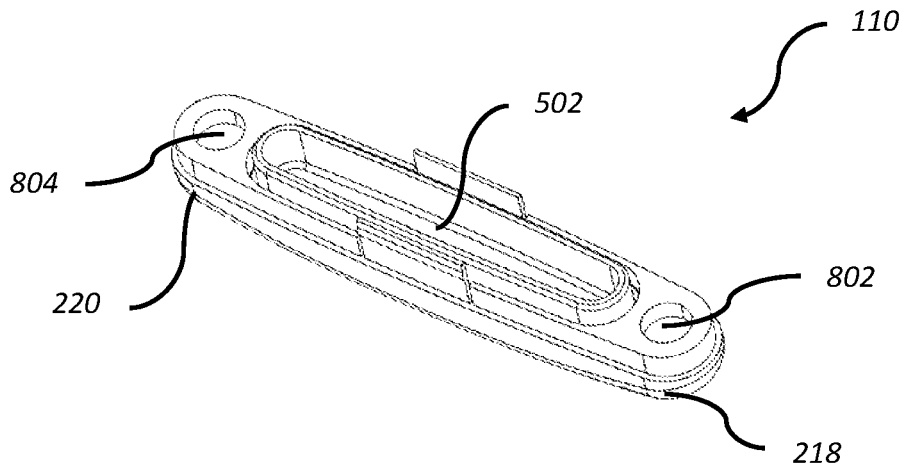
FIG. 8 is a top perspective view of the bottom cap of the dispensing case of FIG. 1.

FIG. 8 is a top perspective view of the bottom cap 110 of the dispensing case 102 of FIG. 1. In particular, FIG. 8 shows holes 802, 804 that may be incorporated on the top of the first and second ends 218, 220 of bottom cap 110. Such holes 802, 804 may receive posts 210, 212 to better secure posts 210, 212 to bottom cap 110.

Figure 9:
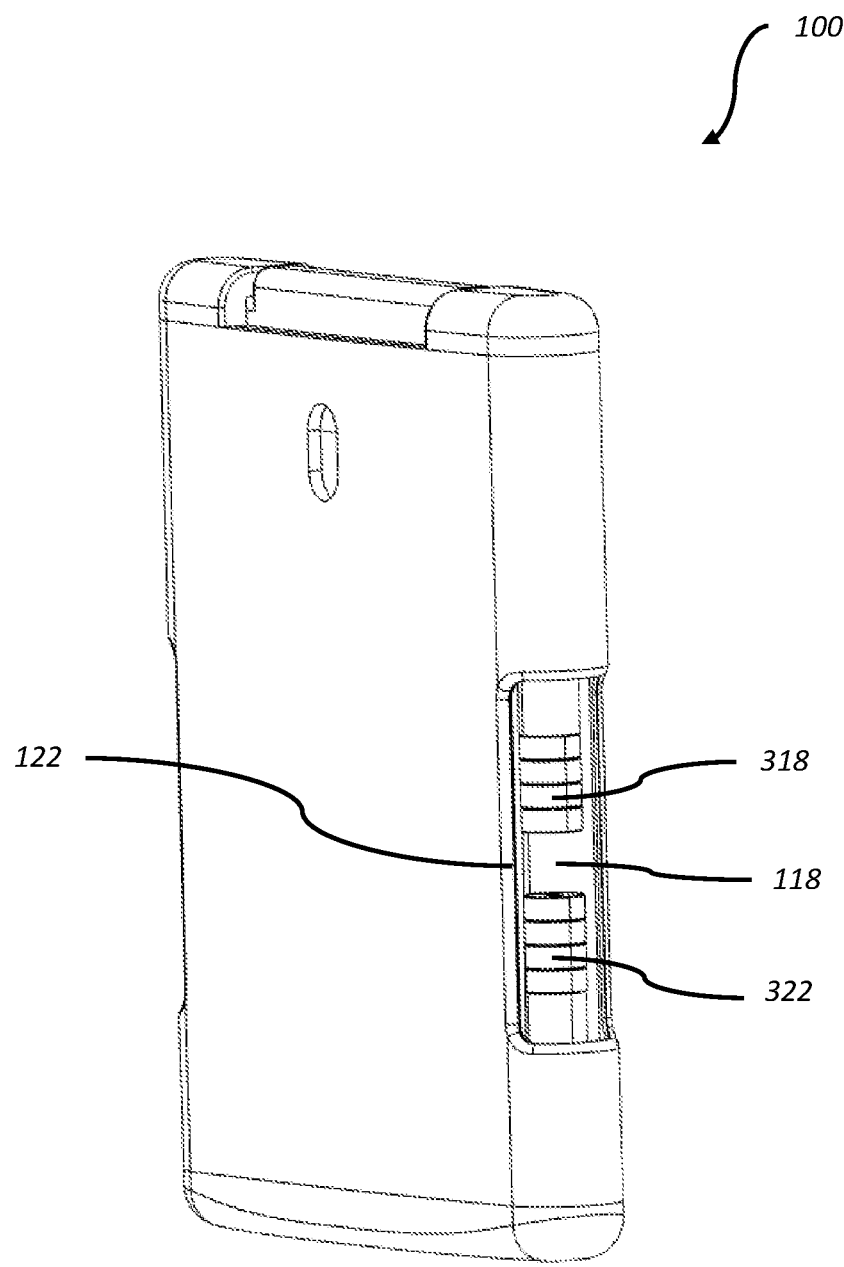
FIG. 9 is a side perspective view of another example of the dispensing device of FIG. 1.

FIG. 9 is another example of a side perspective view of the dispensing device 100 of FIG. 1 where the tubes 118, 120 are made of transparent material, thereby allowing visibility of magnets 318, 320, 322, 324 from the exterior of dispensing device 100. As stated above, tubes 118, 120 may be made of any transparent or semi-transparent material known in the art, including but not limited to acrylic or glass.

Figures 10A, 10B:
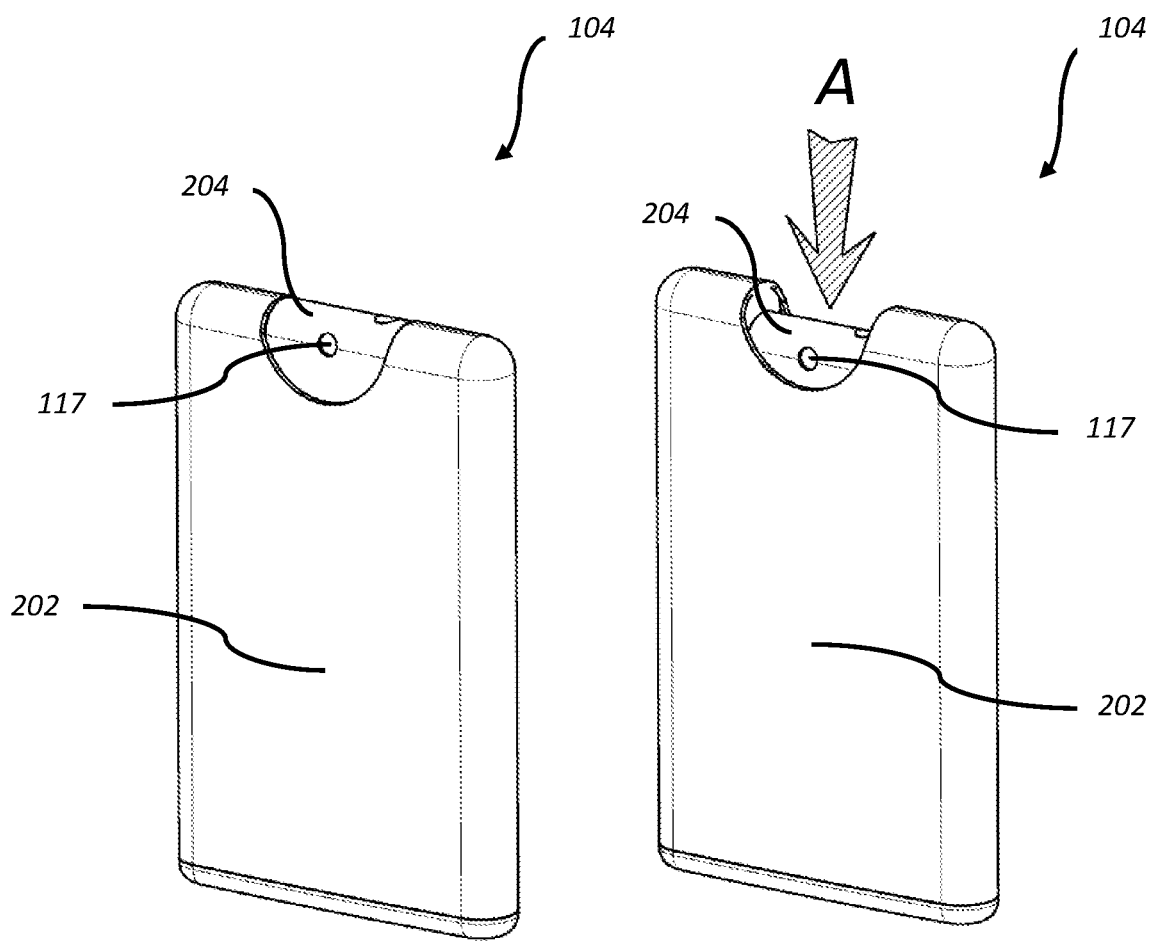
FIG. 10A shows a perspective view of one example of the dispensing cartridge of the dispensing device of FIG. 1 where the actuator is in a first position.
FIG. 10B shows a perspective view of the dispensing cartridge of FIG. 10A where the actuator is in a second position.

FIGS. 10A and 10B show front perspective views of one example of a dispensing cartridge 104 of the dispensing device 100 of FIG. 1 in a first position and in a second position. The dispensing cartridge 104 may comprise of main body 202 and actuator 204 where a dispense hole 117 is located on actuator 204. In this example, main body 202 may hold a reservoir of liquid to be dispensed upon actuation of actuator 204. FIG. 10A shows the actuator 204 in a first position and FIG. 10B shows the actuator 204 in a second position. As shown by arrow A, liquid held within main body 202 may be dispensed through dispense hole 117 upon a user pressing or pushing down on actuator 204. In other words, liquid held within main body 202 may be dispensed when the actuator moves from the first position to the second position. As will be discussed further below, upon a user releasing actuator 204, either a spring and/or at least one pair of top and bottom magnets 318, 320, 322, 324 may move actuator 204 from the second position back to the first position. It should also be understood actuator 112 may move between a first and second position in the same manner as actuator 204.

Dispensing cartridge 104 may be a refillable or replaceable cartridge. Further, dispensing cartridge 104 may comprise of any material intended to be dispensed, including but not limited to hand sanitizing solution, oils, fragrances (e.g. perfumes, colognes etc.), air fresheners, mouth sprays (for freshening breath), water, creams, gels, granules or tablets. Additionally, dispensing cartridge 104 may dispense material in the form of a spray, mist or foam.

Dispensing cartridge 104 may be of any color and can be made from any opaque, transparent or semi-transparent material known in the art, including but not limited to plastic, acrylic or glass. One of the benefits of having the dispensing cartridge 104 transparent or at least semi-transparent is so the user can see how much liquid is left in the cartridge 104 for refilling or cartridge replacement purposes.

Figure 11:
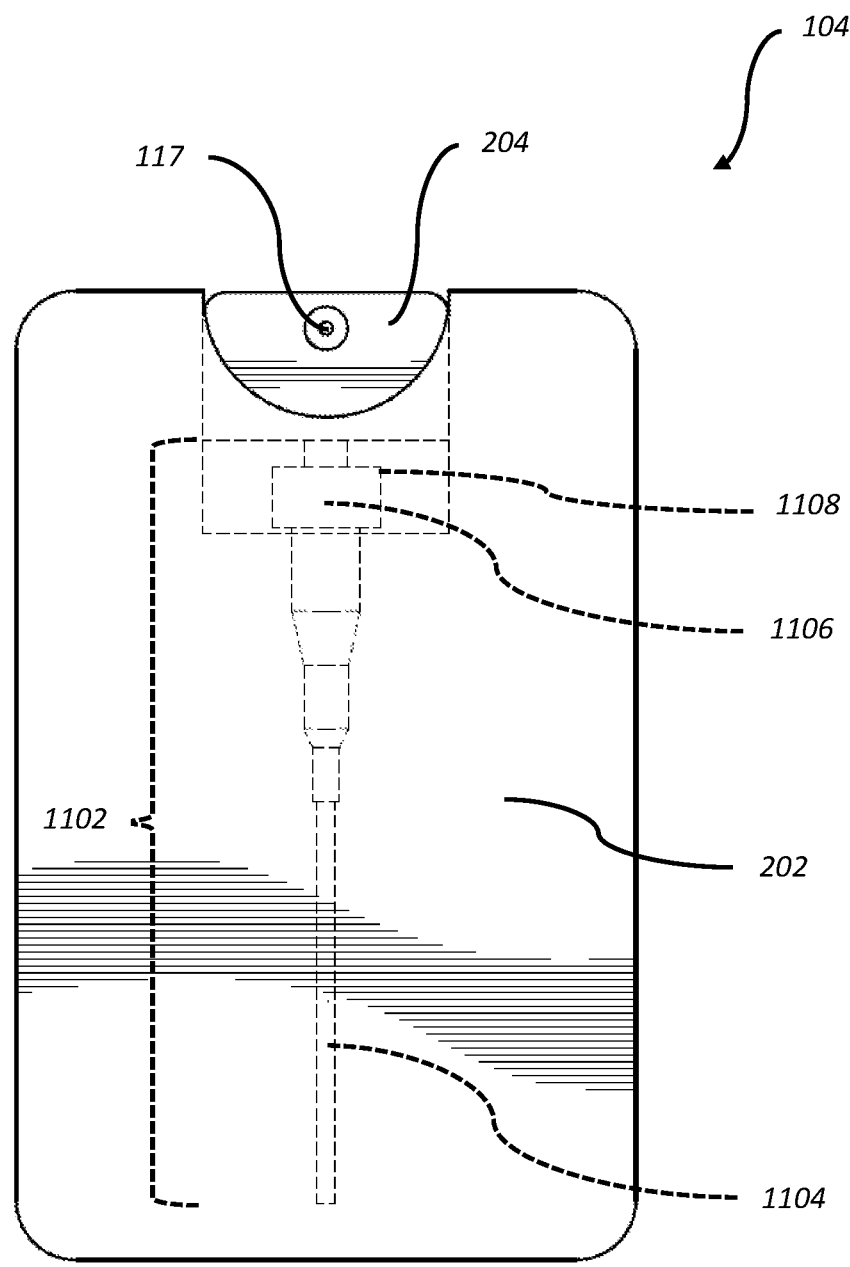
FIG. 11 shows a front view of the dispensing mechanism incorporated in the dispensing cartridge of the dispensing device of FIG. 1.

FIG. 11 shows a front view of the dispensing mechanism incorporated in dispensing cartridge 104 of dispensing device 100 of FIG. 1. In one example, dispensing mechanism 1102 may include a pump mechanism, such as a spring pump, which are commonly known in the art. As commonly known, such spring pumps includes a dip tube 1104, a spring 1106, an actuator 204 and dispense hole 117. Upon pressing down of actuator 204, a pump within the mechanism is activated which draws the liquid in the main body 202 through dip tube 1104 and out the dispense hole 117. The pump is created from a piston (not shown), which is the moving element, that is housed within a cylinder 1108. A spring 1106 is also located within the cylinder 1108. The pump is operated by pressing the actuator 204, which in turn pushes the piston into the cylinder 1108, which in turn compresses the spring 1106. When the actuator 204 is released, the piston is then pushed back out of the cylinder 1108 because of the spring 1106. These two strokes of the piston (into the cylinder and out again) constitutes the pump cycle of the spring pump of dispensing mechanism 1102. As mentioned, such spring pumps are well known in the art. It should also be understood that any mechanism known in the art that incorporates an actuator that must be pressed down to dispense a material can be utilized in connection with dispensing cartridge 104.

In another example of the present invention, the dispensing mechanism of dispensing cartridge 104 may include all of the components of a spring pump as described above absent the spring. In other words, the dispensing mechanism of dispensing cartridge 104 may include a pump mechanism that instead of a spring, relies on the magnetic resistance of magnets 318, 320, 322, 324 for compressing and releasing actuator 204 (the actuator 204 would be attached to actuator 112) and for pushing the piston back out of the cylinder 1108 after actuator 204 is released. In other words, in this pump mechanism example, magnets 318, 320, 322, 324 would substitute the function of a spring to create a pump cycle for dispensing material out from dispensing cartridge 104. The benefits of using magnets as opposed to a spring is that magnets provide much greater durability and allow a much smoother actuation movement of the actuator due to the frictionless magnetic field created between the magnets. Springs have a tendency to malfunction often and the force, strength or resiliency of such springs diminishes much more quickly over time with greater use. Magnets, on the other hand, provide a similar springing-type mechanism, but unlike springs themselves, are much more durable and require much less maintenance. Therefore, the dispensing cartridge 104 described herein may rely on magnets as opposed to a spring for creating a pump and dispensing material.

Figure 12:
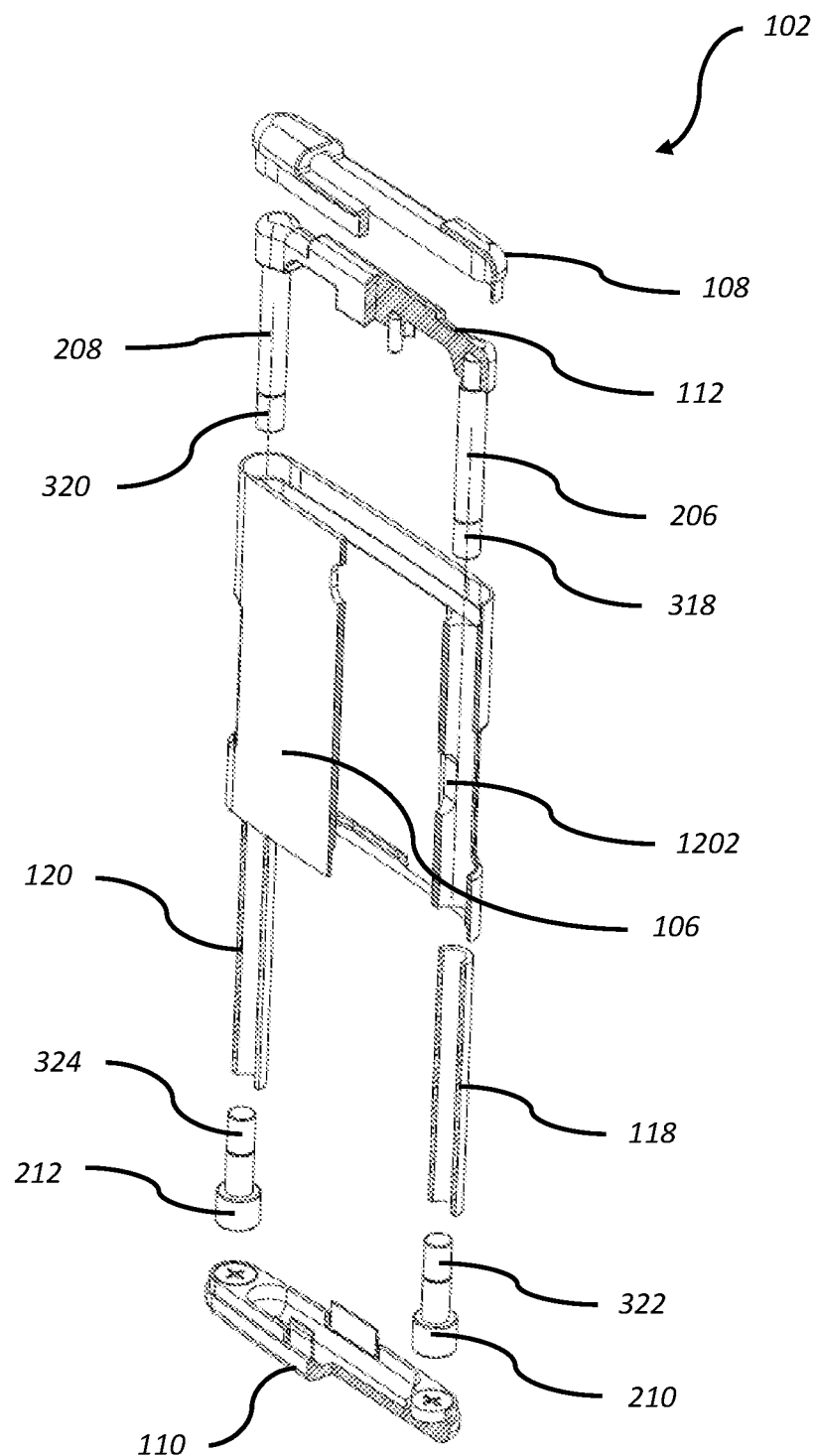
FIG. 12 is a cut away exploded view of the dispensing case of the dispensing device of FIG. 1.

FIG. 12 is a cut away exploded view of the dispensing case 102 of the dispensing device 100 of FIG. 1. As shown, dispensing case comprises a top cap 108, actuator 112, top posts 206, 208 connected to actuator 112, top magnets 318, 320 connected to top posts 206, 208, main body 106, tubes 118, 120, bottom magnets 322, 324 connected to bottom posts 210, 212, and bottom posts 210, 212 connected to bottom cap 110.

As further shown in FIG. 12, main body 106 may comprise of an inner sight window 1202, which allows visibility of the liquid level in the dispensing cartridge 104 so the user can see how much liquid is left in the cartridge 104 for refilling or cartridge replacement purposes. Such inner sight window 1202 may be located at any location on the main body 106, including but not limited to the front or back surface of main body 106.

In one example, to insert, replace or remove the dispensing cartridge 104 from dispensing case 102, the bottom cap 110 may be disconnected from the case 102. Such disconnection can be made from the bottom cap 110 disconnected from bottom posts 210, 212 or from bottom cap 110 together with bottom posts 210, 212 and bottom magnets 322, 324 disconnected from the case 102.

In another example, given that all removeable connections between the various parts or components of the dispensing case 102 described herein can be removably connected by quick-type connections including but not limited to screws, friction fits, press fits, clips, and/or magnets, the dispensing case 102 of the present invention may be highly customizable such that various parts may be interchanged with other similar parts that are of a different material or color. For example, FIG. 12 shows top posts top posts 206, 208 press fitted into the ends of actuator 112. Such top posts 206, 208 may be removably connected to the actuator 112, thus allowing a user to exchange one or more of the top posts 206, 208 with a different color or material. Similar customization may also be done to the bottom posts 210, 212. Additionally, the top and bottom magnets 318, 320, 322, 324 themselves can be removably connected to the top and bottom posts respectively in order to allow a user to not only replace such magnets with different colors but also to add more than two magnets within each tube of tubes 118, 120. For example, if desired, a user may incorporate at least a third magnet that magnetically floats between the top magnets 318, 320 and bottom magnets 322, 324. It is further understood that the top cap 108, actuator 112, main body 106 and bottom cap 110 of the dispensing case 102 may also be customized to any color, material or graphical design/pattern desired.

In addition to serving the purpose of dispensing material, dispensing device 100 may also serve as a platform in which users may desire to place phones, keys or other valuables on, thus providing another sanitary purpose. For example, when eating at a restaurant, restaurant tables are often contaminated with various germs or bacteria. Therefore, it is quite unsanitary for a user to place his or her valuables, such as a mobile phone, directly on the table. Instead, a user may place dispensing device 100 on the table first, and given the dispensing device's flat shape, such device may provide a sanitary platform upon which users may place their valuables on (especially if the dispensing case 102 is made of copper or any other naturally anti-microbial material).

It should further be noted that add-ons may be incorporated on or in connection with the dispensing device 100, including but not limited to money clips, credit card holders, hooks (for contactless pulling of doors or handles), styluses, and bottle openers. Such add-ons may be fixed to the dispensing case 102 or removably connected to the dispensing case 102.

The foregoing description of an implementation has been presented for purposes of illustration and description. It is not exhaustive and does not limit the claimed inventions to the precise form disclosed. Modifications and variations are possible in light of the above description or may be acquired from practicing the invention. The claims and their equivalents define the scope of the invention.

What is claimed is:

1. A dispensing device comprising:
    a dispensing case having a top end and bottom end, where a dispensing case actuator is located at the top end and where a first top magnet is operatively attached to the dispensing case actuator, where a first bottom magnet is attached to the dispensing case and is aligned with the first top magnet, and where the first top magnet magnetically repels the first bottom magnet; and
    a dispensing cartridge housed within the dispensing case, where the dispensing cartridge comprises of a dispensing cartridge actuator operatively connected to a pump mechanism for dispensing liquid held within the dispensing cartridge, where the actuation of the dispensing case actuator from a first position to a second position actuates the dispensing cartridge actuator from a first position to a second position to dispense the liquid in the dispensing cartridge.

2. The dispensing device of claim 1, where the dispensing case is made of a naturally anti-microbial metal material.

3. The dispensing device of claim 1 where the dispensing case actuator includes a push-button.

4. The dispensing device of claim 1 where the first top magnet is attached to the dispensing case actuator via a top post and where the first bottom magnet is attached to the dispensing case via a bottom post.

5. The dispensing device of claim 1 where the dispensing case actuator has a first end and second end, where the first top magnet attaches to the first end of the dispensing case actuator and a second top magnet attaches to the second end of the dispensing case actuator, and where a second bottom magnet is attached to the dispensing case and is aligned with the second top magnet, and where the second top magnet magnetically repels the second bottom magnet.

6. The dispensing device of claim 1 where the first bottom magnet is attached at the bottom end of the dispensing case.

7. The dispensing device of claim 1, where the first top magnet and first bottom magnet are housed within a tube on the dispensing case.

8. The dispensing device of claim 1, where the dispensing cartridge incorporates a pump mechanism that includes a spring.

9. A dispensing device having a dispensing case comprising:
    a main body having a top end and bottom end and an actuator, where a first top magnet is operatively attached to the actuator and a first bottom magnet is attached to the main body, where the first top magnet is aligned with the first bottom magnet and where the first top magnet magnetically repels the first bottom magnet, and where the first top magnet and first bottom magnet are housed within a tube on the main body.

10. The dispensing device of claim 9, where the main body is made of a naturally anti-microbial metal material.

11. The dispensing device of claim 9, where the actuator is located at the top end of the main body.

12. The dispensing device of claim 9, where the actuator moves between a first position and a second position.

13. The dispensing device of claim 12 where the movement from the first position to the second position moves the first top magnet towards the first bottom magnet.

14. The dispensing device of claim 12, where the magnetic repellency of the first top magnet and first bottom magnet moves the actuator from the second position to the first position.

15. A method for dispensing a material, the method comprising the steps of:
    providing a dispensing case, the dispensing case having a top end and bottom end and a dispensing case actuator that moves between a first position and second position, where the dispensing case houses a dispensing cartridge holding a dispensing material, where the dispensing cartridge comprises a dispensing cartridge actuator, where the dispensing case actuator operates with the dispensing cartridge actuator, and where a first top magnet is connected to the dispensing case actuator and a first bottom magnet is attached to the dispensing case and is aligned with the first top magnet, and where the first top magnet magnetically repels the first bottom magnet; and
    moving the dispensing case actuator from the first position to the second position, where moving the dispensing case actuator from the first position to the second position moves the dispensing cartridge actuator from a first position to a second position for dispensing the dispensing material; and
    releasing the dispensing case actuator, where upon releasing the dispensing case actuator, the magnetic repellency between the first top magnet and first bottom magnet moves the dispensing case actuator from the second position to the first position.

16. The method for dispensing a material of claim 15, where the dispensing case actuator has a first end and second end, where the first top magnet attaches to the first end of the dispensing case actuator and a second top magnet attaches to the second end of the dispensing case actuator, and where a second bottom magnet is attached to the body and is aligned with the second top magnet, and where the second top magnet magnetically repels the second bottom magnet.

17. The method for dispensing a material of claim 15, where the dispensing case actuator is attached to the dispensing cartridge actuator, where the dispensing cartridge actuator moves between a first position and a second position, and where the releasing of the dispensing case actuator also moves the dispensing cartridge actuator from the second position to the first position due to the magnetic repellency between the first top magnet and first bottom magnet.

18. The method for dispensing a material of claim 15, where the dispensing cartridge dispenses the material within the dispensing cartridge in the form of a spray.

19. A dispensing device having a dispensing case comprising:
    a main body having a top end and bottom end and an actuator that moves between a first position and a second position, where the actuator has a first end and a second end, where a first top magnet is operatively attached to the first end of the actuator and a second top magnet is attached to the second end of the actuator, and where a first bottom magnet and second bottom magnet is attached to the main body, where the first top magnet is aligned with the first bottom magnet and magnetically repels the first bottom magnet and the second top magnet is aligned with the second bottom magnet and magnetically repels the second bottom magnet.

* * * * *